United States Patent
Wu et al.

(10) Patent No.: US 12,324,840 B2
(45) Date of Patent: Jun. 10, 2025

(54) CD20-TARGETED ANTIBODY COUPLING PHARMACEUTICAL PREPARATION

(71) Applicant: ZHEJIANG TERUISI PHARMACEUTCAL INC., Zhejiang (CN)

(72) Inventors: Youling Wu, Huzhou (CN); Yujie Zhang, Huzhou (CN); Jiali Lu, Huzhou (CN)

(73) Assignee: ZHEJIANG TERUISI PHARMACEUTICAL INC., Zhejiang (CN)

( * ) Notice: Subject to any disclaimer, the term of this patent is extended or adjusted under 35 U.S.C. 154(b) by 730 days.

(21) Appl. No.: 16/486,862

(22) PCT Filed: Feb. 14, 2018

(86) PCT No.: PCT/CN2018/076835
§ 371 (c)(1),
(2) Date: Feb. 25, 2020

(87) PCT Pub. No.: WO2018/149413
PCT Pub. Date: Aug. 23, 2018

(65) Prior Publication Data
US 2021/0130487 A1     May 6, 2021

(30) Foreign Application Priority Data
Feb. 20, 2017   (CN) .......................... 201710088853.9

(51) Int. Cl.
*C07K 16/28* (2006.01)
*A61K 47/68* (2017.01)

(52) U.S. Cl.
CPC .... *A61K 47/6849* (2017.08); *A61K 47/68031* (2023.08); *A61K 47/6883* (2017.08); *C07K 16/2887* (2013.01)

(58) Field of Classification Search
None
See application file for complete search history.

(56) References Cited

U.S. PATENT DOCUMENTS

| | | | |
|---|---|---|---|
| 2003/0082172 A1 | 5/2003 | Anderson et al. | |
| 2005/0180972 A1* | 8/2005 | Wahl ................. | A61K 47/6849 530/391.1 |
| 2012/0003248 A1 | 1/2012 | Doronina et al. | |

(Continued)

FOREIGN PATENT DOCUMENTS

| | | |
|---|---|---|
| CN | 1094965 A | 11/1994 |
| CN | 1938046 A | 3/2007 |

(Continued)

OTHER PUBLICATIONS

Jain et al., Pharm Res (2015) 32:3526-3540 (Year: 2015).*

(Continued)

*Primary Examiner* — Karl J Puttlitz
(74) *Attorney, Agent, or Firm* — Lewis Roca Rothgerber Christie LLP

(57) ABSTRACT

A CD20-targeted antibody coupling pharmaceutical preparation, specifically a preparation comprising a CD20-targeted antibody coupling medication represented by formula I and an excipient. The antibody coupling pharmaceutical preparation has prominent antitumor effect.

9 Claims, 1 Drawing Sheet

(56) References Cited

U.S. PATENT DOCUMENTS

| | | | |
|---|---|---|---|
| 2014/0322233 A1 | 10/2014 | Nam et al. | |
| 2016/0045615 A1* | 2/2016 | Li | A61K 47/40 424/178.1 |
| 2017/0326251 A1* | 11/2017 | Evans | C07K 16/32 |

FOREIGN PATENT DOCUMENTS

| | | |
|---|---|---|
| CN | 102573908 A | 7/2012 |
| CN | 103145847 B | 5/2014 |
| CN | 103254317 B | 8/2014 |
| CN | 108452318 B | 5/2023 |
| WO | 2015/151079 A2 | 10/2015 |
| WO | 2015/151079 A3 | 10/2015 |
| WO | 2016/008112 A1 | 1/2016 |
| WO | 2016/049214 A1 | 3/2016 |

OTHER PUBLICATIONS

Chen et al., Determination of Drug-to-Antibody Ratio for Antibody-Drug Conjugates Purified from Serum, Agilent Technologies, pp. 1-9, 2016 (Year: 2016).*

Agarwal et al., Bioconjugate Chem. 2015, 26, 2, 176-192 (Year: 2015).*

Sun et al., Bioconjug Chem. 2005; 16: 1282-1290 (Year: 2005).*

Li Y et al., J Chromatogr A. 2015; 1393: 81-88 (Year: 2015).*

Protein Concentration and Diafiltration by Tangential Flow Filtration, Millipore Techinical Brief, 2003, downloaded Jun. 7, 2023 from http://wolfson.huji.ac.il/purification/PDF/dialysis/MILLIPORE_TFF.pdf (Year: 2003).*

Teeters et al., Biotechnology and Bioengineering, vol. 108, No. 6, Jun. 2011 (Year: 2011).*

Package Insert Herceptin (Trastuzumab) Genetech, Inc., 2000, downloaded Jun. 7, 2023 from https://www.accessdata.fda.gov/drugsatfda_docs/label/2000/trasgen020900lb.htm (Year: 2000).*

Law et al., Clin Cancer Res (2004) 10 (23): 7842-7851 (Year: 2004).*

Francisco et al., Blood. Aug. 15, 2003;102(4):1458-65 (Year: 2003).*

English Translation of the International Search Report corresponding to PCT/CN2018/076835 mailed May 3, 2018; 6 pages.

Cui, Bing et al., Cirmtuzumab Vedotin (UC-961ADC3), An Anti-ROR1-Monomethyl Auristatin E Antibody-Drug Conjugate, Is a Potential Treatment for ROR1-Positive Leukemia and Solid Tumors, American Society of Hematology, Blood, 2013, 122(21):1637, 2 pages.

Dennler, Patrick et al., "Transglutaminase-Based Chemo-Enzymatic Conjugation Approach Yields Homogeneous Antibody-Drug Conjugates," American Chemical Society, ACS Publications, Bioconjugate Chem., 2014, vol. 25, 569-578.

Francisco, Joseph A. et al., "cAC10-vcMMAE, an anti-CD30-monomethyl auristatin E conjugate with potent and selective anti-tumor activity," The American Society of Hematology, 2003, Blood, vol. 102, No. 4, 1459-1465, 8 pages.

Kozak, Katherine R., Total Antibody Quantification for MMAE-Conjugated Antibody-Drug Conjugates: Impact of Assay Format and Reagents, Bioconjugate Chemistry, 2013, 24,772-779, Supporting Information, 3 pages.

Law, Che-Leung et al., "Efficient Elimination of B-Lineage Lymphomas by Anti-CD20-Auristatin Conjugates," Clinical Cancer Research, 2004, vol. 10, 7842-7851, 10 pages.

Mang, Yuanyi et al., "Efficient elimination of CD 103-expressing cells by anti-CD103 antibody drug conjugates in immunocompetent mice," Elsevier, International Immunopharmacology, 2015, vol. 24, 119-127, 9 pages.

Notification of Grant of Patent Right for Invention issued in corresponding Chinese Application No. 2017100873139 issued Apr. 13, 2023, (1 page) with English translation (2 pages).

Patent Certificate, Application No. 2017100873139, 2 pages.

Wang, Yan-ming et al., Auristatin class antibody drug conjugates: research advances, J Int Pharm Res, vol. 42, No. 4, 427-438, Aug. 2015, 12 pages.

* cited by examiner

CD20-TARGETED ANTIBODY COUPLING PHARMACEUTICAL PREPARATION

FIELD OF THE INVENTION

The present invention relates to the field of bio-medicine and in particular relates to a CD20-targeted antibody coupling pharmaceutical preparation.

BACKGROUND OF THE INVENTION

Lymphomas are a group of malignant tumors that originate from lymph nodes and other lymphoid tissues outside the nodes, with a large variety and high incidence. Every year, tens of thousands of people in China lose their lives due to lymphomas. CD20 is a non-glycosylated quadruple transmembrane phosphoprotein that is specifically expressed on the surface of B lymphocytes, and has important regulatory effects on the differentiation and proliferation of B lymphocytes. The stable and specific expression of CD20 on the surface of B cells makes it an ideal target for the treatment of B cell lymphoma. At present, Rituximab, Zevalin, Bexxar and other anti-CD20 monoclonal antibodies approved by the FDA for the treatment of B-cell lymphoma are marketed.

Antibody-drug conjugate (ADC) belongs to a new type of anticancer drug developed in recent years. It connects antibodies and cytotoxic drugs through conjugates. The targeting effect of antibodies will target cytotoxic drugs to tumor sites. ADC drugs release toxins after entering tumor cells through endocytosis and kill target cells, thereby reducing non-specific systemic toxicity common in drugs used in chemotherapy.

Therefore, those skilled in the art are committed to developing new and more effective antibody-drug conjugates targeting CD20.

SUMMARY OF THE INVENTION

The object of the present invention is to provide a CD20-targeted antibody-drug conjugate pharmaceutical preparation.

Another object of the present invention is to provide a preparation method and use of the antibody-drug conjugate pharmaceutical preparation mentioned above.

In a first aspect of the invention, it provides an antibody-drug conjugate pharmaceutical preparation, wherein the preparation comprises:

(a) antibody-drug conjugate with a structure shown in formula I:

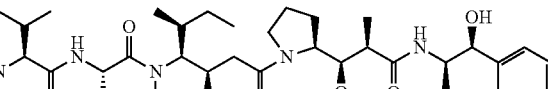

wherein, mAb represents a recombinant anti-CD20 monoclonal antibody, which is rituximab or a biosimilar thereof;

D represents a small molecule toxin, which is one or more monomethyl auristatin;

L is a linker connecting the antibody and the small molecule toxin;

n is the average number of the small molecule toxins conjugated to the antibody; and n is an integer or non-integer of $4.2\pm1$; and "—" is a bond; and (b) a carrier or excipient.

In another preferred embodiment, n is an integer or non-integer of $4.2\pm0.5$.

In another preferred embodiment, n is an integer or non-integer of $4.2\pm0.3$.

In another preferred embodiment, D is monomethyl auristatin-E (MMAE), monomethyl auristatin-D (MMAD), monomethyl auristatin-F (MMAF), or a combination thereof.

In another preferred embodiment, L is maleimidocaproyl-valine-citrulline-p-aminobenzyloxycarbonyl.

In another preferred embodiment, the small molecule toxin is connected to a sulfhydryl group formed after reduction of a disulfide bond between chains of the antibody through a linker.

In another preferred embodiment, the structure of the antibody-drug conjugate is shown as the following formula:

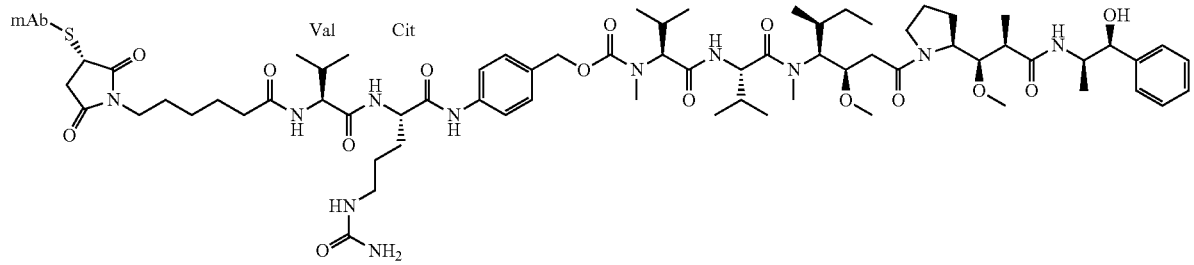

In another preferred embodiment, the preparation is an injection.

In another preferred embodiment, the preparation is a solution or a lyophilized agent.

In another preferred embodiment, the carrier or excipient is selected from the group consisting of a pH buffer, an osmotic pressure regulator, a lyophilized powder excipient, a protein protecting agent, a solubilizer, and water for injection.

In another preferred embodiment, the pH buffer comprises histidine hydrochloride.

In another preferred embodiment, the protein protecting agent comprises trehalose.

In another preferred embodiment, the osmotic pressure regulator comprises mannitol.

In another preferred embodiment, the solubilizer comprises polysorbate 80.

In another preferred embodiment, the preparation method for the antibody-drug conjugate comprises the following steps:

(1) performing a reduction reaction between the recombinant anti-CD20 monoclonal antibody and a reducing agent, thereby obtaining a reaction system comprising a reduced recombinant anti-CD20 monoclonal antibody; and the molar ratio of the monoclonal antibody to the reducing agent is 1:2.9 to 1:3.1; and (2) performing a coupling reaction between the reaction system of step (1) and a solution of a small molecule toxin in acetonitrile and water to form the antibody-drug conjugate according to claim 1; and the molar ratio of the monoclonal antibody in step (1) to the small molecule toxin is 1:7.0 to 1:8.0.

In another preferred embodiment, in step (1), the reduction reaction is performed in a buffer.

In another preferred embodiment, in step (1), the reduced recombinant anti-CD20 monoclonal antibody is a recombinant anti-CD20 monoclonal antibody whose interchain disulfide bond is reduced to sulfhydryl groups.

In another preferred embodiment, in step (1), the reducing agent is tris (2-carboxyethyl) phosphine.

In another preferred embodiment, in step (1), the buffer is a PB reaction buffer (pH7.6).

In another preferred embodiment, in step (1), the molar ratio of the monoclonal antibody to the reducing agent is 1:2.95 to 1:3.05, preferably 1:2.99 to 1:3.01.

In another preferred embodiment, in step (1), the reduction reaction is performed at 25±1° C.

In another preferred embodiment, in step (1), the reduction reaction is performed for 90±10 minutes.

In another preferred embodiment, in step (2), the molar ratio of the monoclonal antibody from step (1) to the small molecule toxin is 1:7.2 to 1:7.7, preferably 1:7.4 to 1:7.6.

In another preferred embodiment, in step (2), the volume ratio of the acetonitrile to water is 1:1.

In another preferred embodiment, in step (2), the coupling reaction is performed at 4±0.5° C.

In another preferred embodiment, in step (2), the coupling reaction is performed for 60±10 minutes.

In another preferred embodiment, in step (2), the mixing step is adding a solution of the small molecule toxin in acetonitrile and water dropwise to the reaction system of step (1).

In a second aspect of the invention, it provides a use of the antibody-drug conjugate pharmaceutical preparation according to the first aspect of the present invention, for preparing anti-tumor drugs.

In another preferred embodiment, the tumor is lymphoma or leukemia.

In another preferred embodiment, the tumor is B-cell non-Hodgkin's lymphoma or chronic lymphocytic leukemia.

In a third aspect of the invention, it provides a non-therapeutic method for inhibiting tumor cells, which comprises the step of adding the antibody-drug conjugate pharmaceutical preparation according to the first aspect of the present invention to a tumor cell-containing system.

In another preferred embodiment, the tumor cells are CD20-positive tumor cells, for example, Raji, Ramos, Daudi cells and the like.

A method for treating or preventing a tumor is also provided in the invention, which comprises the step of administering to a subject in need thereof the antibody-drug conjugate pharmaceutical preparation according to the first aspect of the present invention.

It should be understood that, within the scope of the present invention, the technical features specifically described above and below (such as in the Examples) can be combined with each other, thereby constituting a new or preferred technical solution which needs not be described one by one.

DETAILED DESCRIPTION OF THE INVENTION

Through extensive and intensive researches, the inventors have unexpectedly discovered a CD20-targeted antibody-drug conjugate pharmaceutical preparation with high efficiency and optimized drug-loading capacity. The present invention has been completed on this basis.

Antibody

Antibodies suitable for the present invention are antibodies that target CD20, and are recombinant anti-CD20 monoclonal antibodies. The recombinant anti-CD20 monoclonal antibody may be rituximab, or it may be a biosimilar thereof.

Small Molecule Toxin

Small molecule toxins suitable for the present invention are compounds with high cytotoxicity. Specifically, the small molecule toxin is one or more monomethyl auristatin; more preferably, the small molecule toxin is monomethyl auristatin-E (MMAE), monomethyl auristatin-D (MMAD), monomethyl auristatin-F (MMAF), or a combination thereof.

Wherein, the molecular structure of MMAE is shown below:

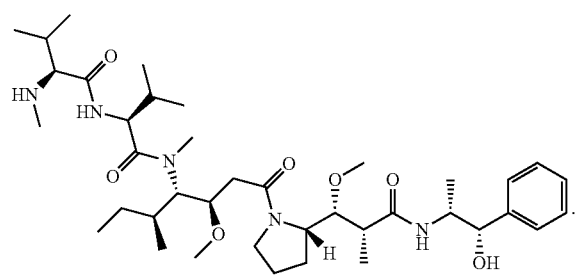 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

Linker

A linker (L) suitable for the present invention is used to connecting the antibody and the small molecule toxin of the present invention. Specifically, the linker is maleimido-caproyl-valine-citrulline-p-aminobenzyloxycarbonyl, such as the one shown in the following formula:

Antibody-Drug Conjugate

An antibody-drug conjugate is provided in the present invention, which comprises (a) a recombinant anti-CD20 monoclonal antibody and (b) a cytotoxic small molecule toxin connected together through a linker (L).

As used herein, the terms "antibody-drug conjugate of the present invention" or "ADC of the present invention" are used interchangeably and refer to a conjugate of an antibody and a small molecule toxin of the present invention connected through a linker.

Specifically, the antibody-drug conjugate has a structure as shown in formula I:

$$\text{mAb-(L-D)n} \qquad \text{I}$$

wherein, mAb represents an antibody of the present invention;

D represents a small molecule toxin of the present invention;

L is a linker connecting the antibody and the small molecule toxin;

n is the average number of the small molecule toxin conjugated to the antibody; and n is an integer or non-integer of 4.2±1; and "—" is a bond.

In another preferred embodiment, n is an integer or non-integer of 4.2±0.5.

In another preferred embodiment, n is an integer or non-integer of 4.2±0.3.

In another preferred embodiment, the structure of the antibody-drug conjugate is shown as the following formula:

mercially available small molecule toxin connected with a linker may also be used.

Then, the free sulfhydryl groups formed by the reduction of four pairs of interchain disulfide bonds of a recombinantly expressed monoclonal antibody molecule is connected with the maleimide group in a linker to which a small molecule toxin has been connected.

Figure 2:
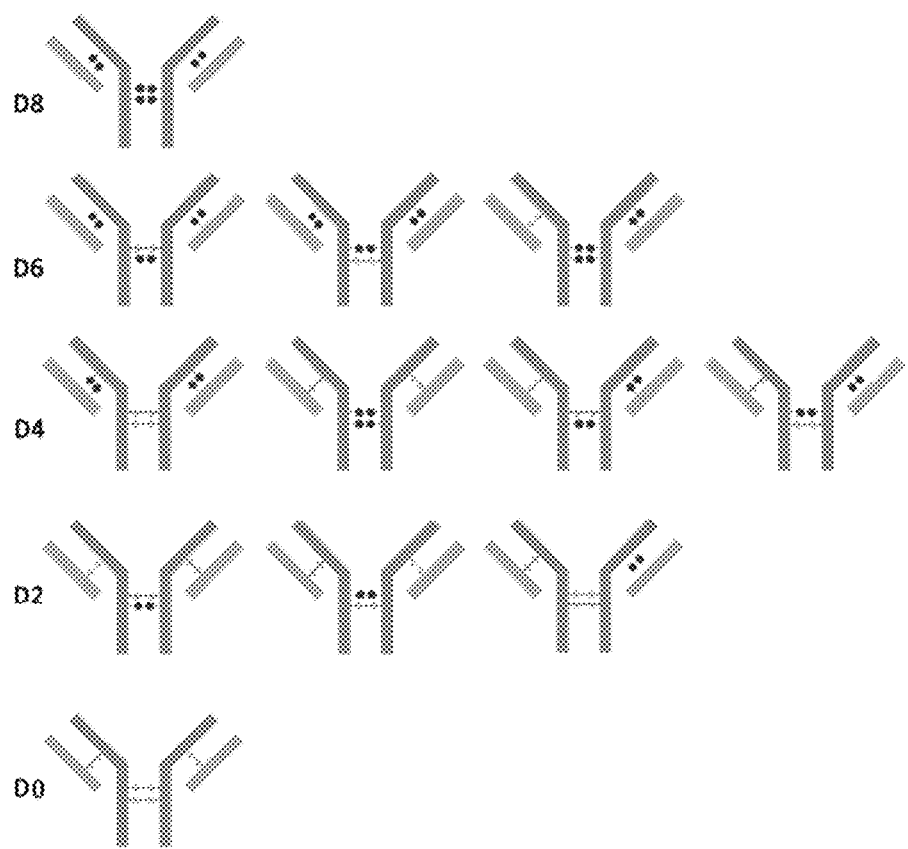
FIG. 2 shows the possible toxin binding sites and drug carrying numbers of the monoclonal antibody-drug conjugate formed.

The resulting monoclonal antibody-drug conjugates have a mixture of multiple drug-loading numbers in solution due to heterogeneity of reaction sites. The possible toxin binding sites and drug loading numbers of the monoclonal antibody-drug conjugates formed are shown in FIG. 2.

It can be known from the above that there are five forms of monoclonal antibody-drug conjugates formed theoretically that carry different numbers of drugs, which are 0, 2, 4, 6, and 8, respectively. In order to evaluate the number of drugs loaded, an internationally accepted evaluation method can be used, that is, counting the average molar ratio of the toxin drugs to antibodies (Drug Antibody Ratio, DAR).

The DAR value of the antibody-drug conjugates of the present invention is an integer or non-integer of 4.2±1; preferably, an integer or non-integer of 4.2±0.5.

Antibody-Drug Conjugate Pharmaceutical Preparation

An antibody-drug conjugate pharmaceutical preparation is also provided in the present invention, which comprises (a) an effective amount of antibody-drug conjugate of the

Preparation Method for the Antibody-Drug Conjugate

A conjugating method for antibody-drug conjugates is provided in the present invention, which conjugates a small molecule toxin to an antibody through a specific linker, and greatly improves the killing activity of the antibody to tumor cells without changing the affinity of the antibody.

First, the small molecule toxin is connected to the linker by conventional chemical synthesis methods, and a compresent invention (as an active ingredient), and (b) at least one pharmaceutically acceptable carrier or excipient.

For preparation, the active ingredient is usually mixed with a carrier or an excipient, or diluted with a carrier or an excipient, or enclosed in a carrier which may be in the form of capsule or sachet. When the excipient acts as a diluent, solid, semi-solid or liquid materials can be used as the excipient. Therefore, the preparation may be a solution, a sterile injectable solution or the like.

Suitable excipients comprise lactose, glucose, sucrose, sorbitol, mannitol, starch, microcrystalline cellulose, polyvinylpyrrolidone, cellulose, water, and the like. Preparations may also comprise wetting agent, emulsifier, preservative (such as methyl and propyl hydroxybenzoate) or the like.

The preparation can be formulated in single-dose or multi-dose form, both of which comprise calculated predetermined amount of the antibody-drug conjugate of the present invention to provide desired therapeutic effect, as well as suitable pharmaceutical excipients.

The preparation can be administered by conventional routes including, but not limited to, intramuscular, intraperitoneal, intravenous, subcutaneous, intradermal, topical administration and the like.

When the preparation is used, a safe and effective amount of the antibody-drug conjugate is administered to a human wherein the safe and effective amount is preferably in the range of 0.001 to 3 milligrams per kilogram of body weight, more preferably in the range of 0.01 to 2 milligrams per kilogram of body weight. Of course, the route of administration, the patient's health status and other factors should be considered for the specific dose, which are within the scope of skills of skilled practitioners.

In addition, the antibody-drug conjugate pharmaceutical preparation of the present invention may further comprises other therapeutic drugs, including but not limited to cyclophosphamide, doxorubicin, vincristine, prednisone, PD1 antibodies, CTLA4 inhibitors, or a combination thereof Use A method for treating mammalian diseases using the antibody-drug conjugate pharmaceutical preparation of the present invention is also provided in the present invention. Preferably, the disease is a CD20 targeting disease such as a tumor, such as a lymphoma (e.g., B-cell non-Hodgkin's lymphoma) or leukemia (chronic lymphocytic leukemia).

The Beneficial Effects of the Present Invention Compared with Prior Arts

A preparation comprising an antibody-drug conjugate with optimized drug-loading capacity and a suitable carrier, diluent or excipient is provided in the present invention. The preparation has high drug activity, high stability, low toxicity, and excellent druggability.

The present invention will be further illustrated below with reference to the specific examples. It should be understood that these examples are only to illustrate the invention, but not to limit the scope of the invention. The experimental methods with no specific conditions described in the following examples are generally performed under the conventional conditions (e.g., the conditions described by US Sambrook et al., Molecular Cloning Laboratory Guide (New York: Cold Spring Harbor Laboratory Press, 1989), or according to the manufacturer's instructions. Unless indicated otherwise, all percentage and parts are calculated by weight. Unless otherwise stated, the raw materials, reagents, cell strains or instruments used in the examples of the present invention are commercially available or conventional.

Example 1 Preparation of Antibody (TRS001)

Coding sequences are fully synthesized based on the amino acid and nucleotide sequences of light and heavy chains of rituximab. The suspension-adapted CHO-K1 (from ATCC, USA) were used as the host cells. Monoclonal antibody light chain (LC) and heavy chain (HC) dual expression plasmids, i.e. pcDNA3-RX-Neo and pcDNA3-RX-GS, were constructed using pcDNA3.0-based expression vector. Both expression plasmids carry genes for the light and heavy chains of the antibody (the light and heavy chains of TRS001 are completely identical to the light and heavy chain sequences of commercially available rituximab) and carry corresponding selection markers. The host cells were co-transfected with the two expression plasmids and stable transfected cells were selected with double selection markers. And then several candidate monoclonal cell lines were screened out step by step using semi-solid medium cloning method. Monoclonal cell lines used for production of antibody (TRS001) were then selected by shaking flask and reactor cultivation.

The monoclonal cell line was sequenced, and sequencing results showed that the sequences encoding the light and heavy chains of TRS001 were completely identical to those of commercially available rituximab. Moreover, the physical and chemical characteristics such as molecular weight of produced rituximab biosimilar are the same as those of rituximab.

The monoclonal cell line selected by the above steps was used as the final production cell line, and a recombinant anti-human CD20 monoclonal antibody TRS001 was prepared by referring to the production method provided by rituximab original medicine patent (CN93121424.6) for subsequent examples.

Example 2 Preparation of Antibody-Drug Conjugate (TRS005, Whose DAR is Approximately 4.2)

1. Preparation of Solutions and Materials

Buffer A: 0.05 mol/L PB Reaction Buffer (pH7.6)

A 0.2 mol/L PB storage buffer (pH 7.6) was prepared using a solution of 0.2 mol/L $NaH_2PO_4 \cdot H_2O$ and 0.2 mol/L $Na_2HPO_4 \cdot 7H_2O$ (using Millipore purified water), filtrated through a 0.22 μm membrane (Nalgene Rapid-Flow Unit) and stored at 4° C., and RT equilibrated and diluted to 0.05 mol/L as a reduction buffer.

Reducing Agent: 100 mmol/L TCEP Solution 1.43 g of TECP (tris (2-carboxyethyl) phosphine) was dissolved in 50 mL of pure water to form a 100 mmol/L solution, which was equally divided to 1 ml/bottle and stored at −80° C.

Buffer B: 10 mg/mL L-Cysteine Termination Buffer 1 g of L-cysteine was dissolved in 100 ml of a 0.1 mM DTPA (diethylenetriaminepentaacetic acid) solution, and the obtained solution was filtered through a 0.22 μm membrane and stored at −80° C.

50% ACN Solution

A 50% acetonitrile solution was prepared by mixing the same volume of ACN and ultrapure water, and filtered through a 0.22 μm membrane and stored at 4 T.

Buffer C: HT Preparation Buffer

1 L HT preparation buffer contains 3.18 g of L-histidine, 70 g of trehalose dihydrate, and 0.2 mL of Tween 80. The pH was adjusted to 6.5 using 0.5 mol/L hydrochloric acid, and the obtained buffer was filtered through a 0.22 μm membrane and stored at 4° C.

2. Reduction of TRS001 (Molar Ratio: mAb:TCEP≈1:3)

The TRS001 stock solution (55 mg/mL) prepared in Example 1 was thawed at 25° C. overnight (stabilization chamber). 1616 mL of buffer A was added in a reactor (the reactor was pre-filled with 0.1 mol/L NaOH for more than 24 hours and cleaned), then 2 mL of 100 mmol/L TCEP solution was added and mixed (100 rpm, 5 minutes). 182 mL of TRS001 stock solution was added and stirred at 100 rpm, and the reduction reaction continued at 25° C. for 90 min.

3. Binding (Molar Ratio: mAb:vcMMAE≈1:7.5)

The temperature-controlled reaction bath was set to 4° C. (added with ice for cooling). The stirring speed was kept at 100-200 rpm. 13.2 mL of vcMMAE (50 mg/mL) (purchased from Levena Biopharma company) was added to 186.8 mL of 50% ACN, and then the solution was carefully added through the sample addition tube and mixed very slowly (the sample addition time was controlled within 10 min). All the materials were gently dropped into the reaction system obtained from the above steps. The reaction time was maintained for 1 h after the vcMMAE solution was completely fed.

4. Termination of the Reaction 10 mL of buffer B was added into the reactor within 10 minutes to stop the conjugating reaction. After the conjugating reaction was stopped, the next step of buffer replacement was performed.

5. Buffer Replacement

The conjugating solution was transferred to a TFF system (pre-soaked with 0.1 mol/L NaOH and cleaned). Buffer A was changed to buffer C and then filtrated with a 0.22 microliter Rapid-Flow device. The residual rate of buffer A in the final solution should be less than 0.25%. The TRS005 stock solution after buffer replacement can be stored at 2-8° C.

Figure 1:
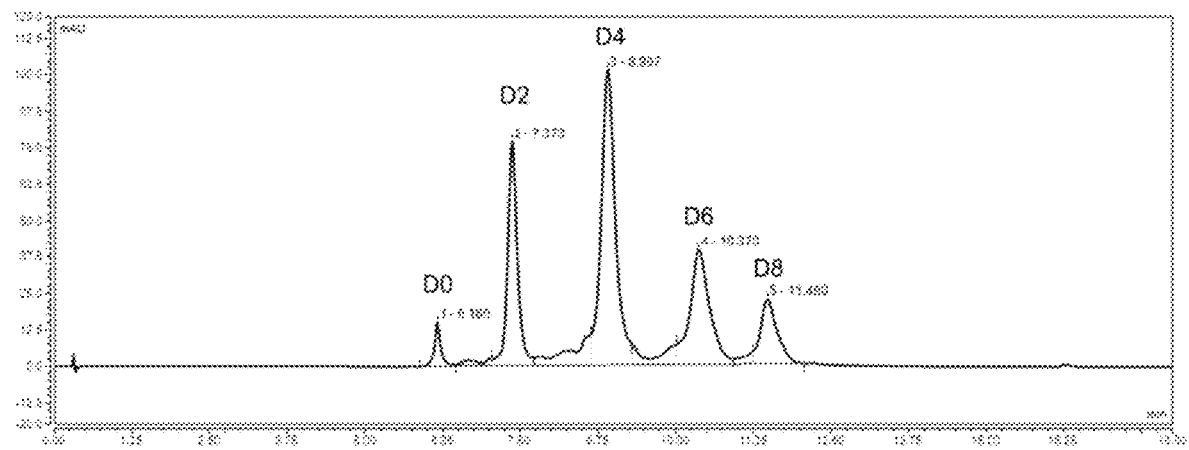
FIG. 1 is a hydrophobic interaction chromatogram to identify the drug-loading capacity of antibody-drug conjugate TRS005.

Finally, the antibody-drug conjugate TRS005 with a DAR of about 4.2 was obtained. The result of identification of drug-loading capacity of the antibody-drug conjugate was shown in FIG. 1.

Example 3 Lyophilized Preparation of Recombinant Anti-CD20 Monoclonal Antibody-Drug Conjugate Preparation Comprises:

Rituximab, histidine hydrochloride, alginic acid, mannitol, polysorbate 80, and water for injection.

The obtained preparations were tested by stability experiments and the results indicate that they fully meet the requirements of pharmaceutical preparations.

All the documents cited herein are incorporated into the invention as reference, as if each of them is individually incorporated. Further, it would be appreciated that, in light of the above described teaching of the invention, the skilled in the art could make various changes or modifications to the invention, and these equivalents would still be in the scope of the invention defined by the appended claims of the application.

The invention claimed is:

1. A preparation method of an antibody-drug conjugate with a structure as shown in formula I:

mAb-(L-D)n     I wherein,
mAb represents a recombinant anti-CD20 monoclonal antibody, wherein the recombinant anti-CD20 monoclonal antibody is rituximab or a biosimilar thereof;
D represents a small molecule toxin, wherein the small molecule toxin is monomethyl auristatin-E (MMAE);
L is a linker connecting the antibody and the small molecule toxin, wherein the linker is maleimidocaproyl-valine-citrulline-p-aminobenzyloxycarbonyl;
n is an average number of the small molecule toxins conjugated to the antibody, and n is in a range of 4.2±0.5; and
"-" is a bond, and wherein the structure of the antibody-drug conjugate is the following formula:

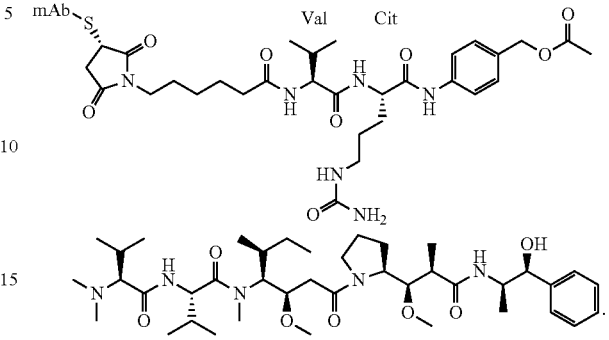

and wherein the preparation method comprises the steps of:
(1) performing a reduction reaction between the recombinant anti-CD20 monoclonal antibody and a reducing agent in a PB (phosphate buffer) reaction buffer (pH 7.6) at 25±1° C. for 90+10 minutes, thereby obtaining a reaction system comprising a reduced recombinant anti-CD20 monoclonal antibody, wherein the reducing agent is tris (2-carboxyethyl) phosphine, and a molar ratio of the recombinant anti-CD20 monoclonal antibody to the reducing agent is 1:2.9 to 1:3.1;
(2) adding a solution of maleimidocaproyl-vc-PAB-MMAE in acetonitrile and water dropwise to the reaction system of step (1) and performing a coupling reaction at 4+0.5° C. for 60+10 minutes to obtain a coupling solution, wherein a volume ratio of acetonitrile to water is 1:1, and a molar ratio of the recombinant anti-CD20 monoclonal antibody in step (1) to the small molecule toxin is 1:7.0 to 1:8.0;
(3) adding into the reaction system obtained from step (2) a stopping solution of L-cysteine which is prepared by dissolving L-cysteine in a diethylenetriaminepentaacetic acid solution, to terminate the coupling reaction; and
(4) when the coupling reaction in step (3) is terminated, transferring the coupling solution to a tangential flow filtration (TFF) system for buffer replacement, thereby replacing the PB reaction buffer with a HT preparation buffer, and filtering the solution obtained with a 0.22 micrometer Rapid-Flow device to make a residual rate of the PB reaction buffer in a final solution less than 0.25%, wherein the HT preparation buffer contains 3.18 g of L-histidine, 70 g of trehalose dihydrate, and 0.2 mL of Tween 80 per L, with pH adjusted to 6.5 using 0.5 mol/L hydrochloric acid, and then filtered through a 0.22 μm membrane.

2. The preparation method of claim 1, wherein n is in a range of 4.2+0.3.

3. The preparation method of claim 1, wherein in step (1), the molar ratio of the recombinant anti-CD20 monoclonal antibody to the reducing agent is about 1:2.95-1:3.05.

4. The preparation method of claim 1, wherein in step (1), the molar ratio of the recombinant anti-CD20 monoclonal antibody to the reducing agent is about 1:2.99-1:3.01.

5. The preparation method of claim 1, wherein in step (1), the molar ratio of the recombinant anti-CD20 monoclonal antibody to the reducing agent is about 1:3.

6. The preparation method of claim 1, wherein in step (2), the molar ratio of the recombinant anti-CD20 monoclonal antibody from step (1) to the small molecule toxin is about 1:7.2-1:7.7.

7. The preparation method of claim 1, wherein in step (2), the molar ratio of the recombinant anti-CD20 monoclonal antibody from step (1) to the small molecule toxin is about 1:7.4-1:7.6.

8. The preparation method of claim 1, wherein in step (2), the molar ratio of the recombinant anti-CD20 monoclonal antibody from step (1) to the small molecule toxin is about 1:7.5.

9. The preparation method of claim 1, wherein n is 4.2, and
- in step (1), the reduction reaction between the recombinant anti-CD20 monoclonal antibody and the reducing agent is performed in the PB reaction buffer (pH 7.6) at 25° C. for 90 minutes, the molar ratio of the recombinant anti-CD20 monoclonal antibody to the reducing agent is 1:3; and
- in step (2), the solution of the small molecule toxin in acetonitrile and water is dropwise added to the reaction system of step (1) and the coupling reaction is performed at 4° C. for 60 minutes, and the molar ratio of the recombinant anti-CD20 monoclonal antibody in step (1) to the small molecule toxin is 1:7.5.

\* \* \* \* \*